United States Patent

Becker et al.

Patent Number: 5,288,886
Date of Patent: Feb. 22, 1994

[54] METHOD OF PREPARING TRIALKYL-TIN HYDRIDES

[75] Inventors: Ralf-Jurgen Becker, Hamm; Ulrich Stewen, Schwerte; Udo Weinberg, Bergkamen, all of Fed. Rep. of Germany

[73] Assignee: Witco GmbH, Bergkamen, Fed. Rep. of Germany

[21] Appl. No.: 86,671

[22] Filed: Jul. 1, 1993

[30] Foreign Application Priority Data

Jul. 17, 1992 [DE] Fed. Rep. of Germany ....... 4223615

[51] Int. Cl.$^5$ ................................................ C07F 7/22
[52] U.S. Cl. ...................................... 556/102; 556/87; 556/95
[58] Field of Search ............................ 556/87, 95, 102

[56] References Cited

U.S. PATENT DOCUMENTS

| | | | |
|---|---|---|---|
| 3,401,183 | 9/1968 | Berger | 260/429 |
| 3,439,008 | 4/1969 | Berger | 260/429 |
| 4,282,166 | 9/1981 | Liauw et al. | 260/429.7 |

FOREIGN PATENT DOCUMENTS

| | | |
|---|---|---|
| 1468709 | 10/1962 | Fed. Rep. of Germany . |
| 1167345 | 4/1964 | Fed. Rep. of Germany . |
| 3119643 | 5/1981 | Fed. Rep. of Germany . |
| A41412 | 6/1988 | Hungary . |
| 0006737 | 4/1966 | Japan . |
| 0002417 | 2/1967 | Japan . |

OTHER PUBLICATIONS

Chemical Abstracts, vol. 108, No. 17, Chem. Abs. No. 150719d, p. 772 (1988).
Chemical Abstract No. 90: 204205p (1979).
Chemical Abstract No. 70: 37922y (1969).
K. Hayashi, et al., *J. Organometal Chem.* 10 (1967), 81-94.
E. Birnbaum, et al., *J. Organometal. Chem.* 9 (1967), 379-382.
H. J. Albert, et al., Methodicum Chimicum vol. 7, Part A, New York, Academic Press, 1977, 361-62.
Chemical Abstract No. 69: 106880b (1968).
Chemical Abstract No. 69:106879h (1968).

*Primary Examiner*—José G. Dees
*Assistant Examiner*—Porfirio Nazario-Gonzalez
*Attorney, Agent, or Firm*—Scully, Scott, Murphy & Presser

[57] ABSTRACT

The invention concerns a method of preparing trialkyltin hydrides by a process that ensures outstanding long-term stability.

Bis-[trialkyl-tin]oxides are dissolved in a solvent that mixes only to some extent, if at all, with water and converted with an aqueous solution of sodium borohydride stabilized with a base. The product is obtained by phase separation and optionally by distillation. The trialkyl-tin hydride is obtained almost quantitatively with a yield of more than 95%.

13 Claims, No Drawings

METHOD OF PREPARING TRIALKYL-TIN HYDRIDES

FIELD OF THE INVENTION

The present invention relates to an improved method of preparing trialkyl-tin hydrides of the general formula $R_1R_2R_3SnH$ wherein $R_1$, $R_2$, and $R_3$ are the same or different branched and/or unbranched and/or substituted alkyls having from about 1 to about 18 carbon atoms. The particular process of the claimed invention ensures that the trialkyl-tin hydrides will remain stable under normal storage conditions for a longer period of time than previously reported.

BACKGROUND OF THE INVENTION

Organo-tin hydrides, especially tri-n-butyl-tin hydride, are valuable organic-synthesis reagents with an extraordinarily wide range of applications. These compounds are highly selective reducing agents Furthermore, the organo-tin hydrides may be used, for example, as catalyst, stabilizers, or biocides. The value and importance of these compounds has been demonstrated in a number of publications. Detailed information can be obtained from such reviews as W. P. Neumann, Synthesis 1987, 655; B. Giese, Radicals in Organic Synthesis: Formation of Carbon Bonds, Oxford, Pergamon Press, 1986; M. Pereyre, J. P. Quintard, & A. Rahm, Tin in Organic Synthesis, London, Butterworth, 1987; D. P. Curran, Synthesis 1988, 417 & 489; I. Omar, Organotin Chemistry, Amsterdam, Elsevier, 1989; and P. G. Harrison, Chemistry of Tin, Glasgow & London, Blackie, 1989.

Despite the wide range of applications reported in the prior art for these compounds, industrial use has been restricted by the limited stability of the organo-tin hydrides, which subsequently is a direct result of unsatisfactory preparation and purification techniques employed in prior art processes.

The instability of the organo-tin hydrides is caused by trace quantities of contaminants that remain in the product even after separation and extraction. Such trace amounts of contaminants are known to hinder the production of the hydrides and/or directly catalyze their decomposition. For example, traces of Lewis acids such as aluminum, boron, and organo-aluminum and organo-tin halogenides are known to trigger immediate decomposition of the resultant organo-tin hydride compound.

Some methods of stabilizing these organo-tin hydrides subsequently have been published. Such methods are disclosed, for example, in German Patent No. 1 167 345 & German, Patent No. 1 468 709. These references disclose purification of the organo-tin hydride compound by additional extraction with alcohols or basic solutions. However, this additional extraction method is inefficient and results in unacceptably low yields of product.

Other methods of preparing organo-tin hydrides have also been described in the prior art, however, these methods contain the above-mentioned drawbacks and/or result in low yields of the organo-tin hydrides. These methods of preparing organo-tin hydrides are illustrated hereinbelow.

U.S. Pat. No. 4,282,166 describes a method of preparing trialkyl-tin hydrides from trialkyl-tin chloride and sodium bis-(2-alkoxyethoxy) aluminum dihydride.

Chemical Abstract No. 90: 204 205p describes reducing trialkyl-tin chloride with sodium borohydride ($NaBH_4$) in mixtures of ether and water. Yields of about 65 to 80% are obtained by employing this particular method.

U.S. Pat. No. 3,439,010 describes obtaining yields of approximately 80% trialkyl-tin hydrides by thermally decomposing trialkyl-tin formiates.

The preparation of organo-tin hydrides from sodium hydride and alkyl-tin chlorides is described in U.S. Pat. No. 3,401,183.

Alkyl-tin oxides and chlorides can be converted into tin hydrides with siloxanes and silanes. This process is described in the following references: K. Hayashi, et al., J. Organomet. Chem. 10, 1, 81-94; Japanese Patent 43 010 134 [Chemical Abstr. No. 69: 106 880 b]; Japanese Patent 43 010 133 [Chemical Abstr. No. 69: 106 879 h]; Japanese Patent 43 012 132 [Chemical Abstr. No. 70: 37 922 y]; and German Patent 3 119 643.

H. J. Albert, T. N. Mitchell, and W. P. Neumann in H. Zimmer, ed., Methodicum Chimicum Vol. 7, Part A, New York, Academic Press, 1977, 361-62 describes the use of aluminum lithium hydride ($LiAlH_4$) which subsequently yields 66 to about 89% trialkyl-tin hydrides.

Satisfactory yields can be obtained by reacting trialkyl-tin chlorides with sodium borohydride, although the reaction and preparation are complicated and difficult. This particular reaction is described in J. Organomet. Chem. 9, 2, 379-82 (1967).

Hungarian Patent A-41-412 describes a method of preparing tri-n-butyl-tin-hydride from bis-[tri-n-butyl-tin]oxide. The process is characterized by dissolving the oxide in an aliphatic alcohol and reacting the mixture at 10° to 30° C. with an alcoholic and/or aqueous solution of sodium borohydride for 10 to 60 minutes. Yields of 64 to 84% tri-n-butyl-tin hydride are isolated subsequent to a complicated series of purifications.

Despite the numerous methods available in the art, continual research is ongoing in an attempt to provide an easier method of preparing organo-tin hydrides which are stable under normal storage conditions over a longer period of time.

SUMMARY OF THE INVENTION

It has, surprisingly, now been discovered that trialkyl-tin hydrides of the general formula $R_1R_2R_3SnH$ wherein $R_1$, $R_2$, and $R_3$ are the same or different branched and/or unbranched and/or substituted alkyls having from about 1 to about 18 carbons can be prepared in a simple and reliable reaction that comprises the steps of:

a) reducing bis-[trialkyl-tin]oxide with a stabilizing aqueous solution of sodium borohydride in the presence of an inert solvent that mixes only to some extent, if at all, with water, b) maintaining the reaction temperature between about 0° to about 100° C. and preferably between 20° and 60° C., c) allowing the batch to stand for about 0 to about 3 hours subsequent to separation thereof, d) separating the organic phase from the aqueous phase, and e) obtaining the product by distilling the solvent off.

The method described hereinabove results in higher yields of high-purity organo-tin hydrides from relatively inexpensive and easily obtained starting compounds. Furthermore, the product is, essentially free from decomposition initiators and promoters which is apparently due to the present method's extraction and neutralization effect.

DETAILED DESCRIPTION OF THE INVENTION

In accordance with the method of the present invention, highly stable trialkyl-tin hydrides are prepared by initially reducing bis-[trialkyl-tin]oxide with a stabilized aqueous solution of sodium borohydride in the presence of an inert solvent that mixes slightly with water.

The mixture containing the bis-[trialkyl-tin]oxide and stabilized sodium borohydride solution is reacted at a temperature of about 0° to about 140° C. More preferably, the temperature of the reduction reaction is from about 20° to about 60° C. The reaction mixture is then held at the desired temperature for a period of about 0 to 3 hours.

In accordance with a preferred embodiment of the present invention, an inert solvent that does not react with either organo-tin hydrides or sodium borohydride is employed. Suitable inert solvents that may be employed by the present invention include diethylether, dioxane, acetonitrile, and hydrocarbons. Tetrahydrofuran is most particularly preferred. The starting compounds which are employed by the claimed invention are preferably introduced stoichiometrically or almost stoichiometrically at ratios of about 0.5 to about 1.5 moles of sodium borohydride per mole of bis-[trialkyl-tin]oxide.

The method of the claimed invention can be further facilitated by using a stabilized aqueous solution of sodium borohydride. Bases such as sodium hydroxide are particularly preferred for this purpose.

The reaction can also be accelerated by adding about 0.1 to about 10% by weight of a hydrogen-acid compound to the reaction mixture containing the bis-[trialkyl-tin]oxide and the stabilized sodium borohydride solution. Suitable hydrogen-acid compounds that can be employed to accelerate the present reaction include thiosalicylic acid, lactic acid, dodecanethiol, thioglycolic acid and the like. Of these hydrogen acid compounds, thioglycolic acid is most particularly preferred.

The reduction of the bis-[tri-alkyl-tin]oxide can also be advantageously accelerated by adding about 0.1 to about 10% by weight of antioxidants. Typical antioxidants employed by the present invention included radical traps such as butylated hydroxytoluene (BHT), 3-tert-butyl-4-hydroxyanisole, pyrogallol, and metal-ion deactivators such as triphenylphosphine, 4,4-thio-bis-(2-tert-butyl-5-methylphenol), ethylenediamine N,N,N',N'-tetra-2-propyl alcohol, and N',N'-diphenyl-1,4-phenylenediamine.

As mentioned previously hereinabove, the method of the claimed invention is easier and more reliable than previously published methods. Furthermore, the starting materials employed by the claimed process are cheaper and more cost-effective than prior art starting materials.

Moreover, the reaction of bis-[trialkyl-tin]oxides with a stabilized aqueous solution of sodium borohydride is simple to regulate. Regulation of the reaction is simply achieved by adding controlled quantities of the reductant. If desired, the reaction can be reversed without decreasing the overall yield of the product. It should be noted that the reaction of the instant invention can be conducted both continuously or discontinuously.

When the starting materials are mixed together, two different and distinct liquid phases appear. The upper, organic phase which appears contains the trialkyl-tin hydride, as well as the unconverted bis-[trialkyl-tin]oxide. The lower, aqueous phase, contains the reductant, sodium borohydride, and its oxidation product(s).

Since the reaction of the claimed invention is liquid in liquid, any contaminants that enter with the starting materials will be constantly extracted from the organic phase. For example, any traces of Lewis acids, which subsequently catalyze the decomposition of organo-tin hydrides, will be neutralized by the basic sodium-borohydride solution and will enter the lower aqueous phase.

Furthermore, auxiliary compounds such as hydrogen-acid compounds or antioxidants that tend to accelerate the reaction will also be eliminated from the organic phase and will not contaminate the trialkyl-tin hydrides.

The yields of the present invention are almost quantitative because the depletion of the contaminants in the reaction mixture starts simultaneously with the reduction process.

The termination of reduction process is followed by separation of the lower, aqueous phase, wherein sodium borohydride can be re-employed. The solvent is then distilled from the upper, organic phase, which contains the organo-tin hydride. Further purification of the product is unnecessary.

The particular advantage of the claimed method is that the extraction and neutralization performed by the basic aqueous phase makes it possible to prepare trialkyl-tin hydrides of high purity and in almost quantitative yields. The hydrides will be free of decomposition initiators and/or catalysts. Moreover, no additional purification processes are required by the present invention. More importantly, the tin hydrides produced by the instant invention are extremely stable under normal storage conditions even after a long period of time. The increased stability of the compounds of the present invention is believed to be caused by the absence of any decomposition initiators and/or catalysts which cause decomposition of the trialkyl-tin hydride compounds. Thus, the compounds of the present invention are suitable for a wide range of industrial application such as catalyst, stabilizers, reducing agents or biocides.

The following examples are given to illustrate the scope of the present invention. Because these examples are given for illustrative purposes, only the invention embodied therein should not be limited thereto.

EXAMPLES

Example 1

810 g of bis-[tributyl-tin]oxide are mixed with 2.5% by weight of thioglycolic acid and dissolved in 600 g of tetrahydrofuran. A solution of 51.5 g of sodium borohydride in 130 g of water and stabilized with 12 g of sodium hydroxide (NaOH) is added at 60° C. within 30 minutes. The tetrahydrofuran is distilled off, the aqueous phase separated, and 770 g (97%) of product is isolated.

Example 2

1 to 5% by weight of such antioxidants as butylated hydroxytoluene, hydroquinone, or pyrogallol is of advantage when reduction occurs without a protective atmosphere.

The conversion is similar to the conversion described in Example 1, however, 3% of butylated hydroxytoluene is added. Bis-[tributyl-tin]hydride is isolated almost quantitatively.

Example 3

135 g of bis-[tributyl-tin]oxide and 3.4 g of thioglycolic acid are added to 100 g of acetonitrile. 8.5 g of sodium borohydride, dissolved in 20 g of water and stabilized with 1.0 g of sodium hydroxide, are added at 20° C. The temperature rises to approximately 38° C. The reaction is allowed to continue for 1 hour. Thereafter, phases are separated and 123 g (93%) of product is isolated therefrom by fractionated distillation.

Example 4

Conversion is conducted as described in Example 3; however, dioxane is employed as the solvent.

Example 5

51 g of sodium borohydride is dissolved in 150 ml of water. The batch is stabilized with 12 g of sodium hydroxide and solved in 600 g of tetrahydrofuran. 810 g of bis-[tributyl-tin]oxide and 34.8 g of thiosalicylic acid are then added. The organic phase is separated and employed for distillation. The yield of tri-n-butyl-tin hydride is 770 g (97%).

Example 6

The reaction conditions are similar to those in Example 5 except that the accelerator is lactic acid instead of thiosalicylic acid.

Example 7

The reaction conditions are similar to those in Example 5 except that the accelerator is dodecanethiol instead of thiosalicylic acid.

Example 8

306 g of bis-[tributyl-tin]oxide and 257 g of tetrahydrofuran are stabilized with 0.025% of butylated hydroxytoluene. A solution of 14.6 g of sodium borohydride in 50 ml of 1 n sodium hydroxide is added at 40° C. The batch is left for 1 hour at 50° C. and treated as hereintofore described. 290 g (96%) of tri-n-butyl-tin hydride are isolated.

Example 9

306 g of bis-[trioctyl-tin]oxide and 257 g of tetrahydrofuran are stabilized with 0.64 g of butylated hydroxytoluene. A solution of 12.4 g of sodium borohydride in 50 ml of 1 n aqueous sodium-hydroxide solution is added at 40° C. The batch is left for 2 hours at 50° C. and treated as hereintofore described. 300 g (100%) of trioctyl-tin hydride are isolated.

Example 10

9.3 g of sodium borohydride in 25 g of water stabilized with 2.2 g of sodium hydroxide are treated with 150 g of tetrahydrofuran stabilized with 0.025% of butylated hydroxytoluene. 189 g of bis-[trihexyl-tin]oxide and 3.7 g of thioglycolic acid are added at room temperature. The batch is left for 10 minutes at 65° C. and cooled. The organic phase is separated. Fractionation is followed by isolation of 170 g (92%) of trihexyl-tin hydride.

Example 11

Trineophyl-tin hydride is prepared by a method similar to that described in Example 10.

Example 12

Tri-isobutyl-tin hydride is prepared by a method similar to that described in Example 10.

The above embodiments and examples are given to illustrate the scope and spirit of the present invention. These embodiments and examples will make apparent, to those skilled in the art, other embodiments and examples. These other embodiments and examples are within the contemplation of the present invention; therefore, the instant invention should be limited only by the appended claims.

What is claimed is:

1. A method of preparing trialkyl-tin hydrides of the general formula $R_1R_2R_3SnH$, wherein $R_1$, $R_2$, and $R_3$ are the same or different branched and/or unbranched and/or substituted alkyls having from about 1 to about 18 carbon atoms, comprising the steps of:
   a) reducing bis-[trialkyl-tin]oxide with a stabilized aqueous solution of sodium borohydride in the presence of an inert solvent that mixes only to some extent, if at all, with water,
   b) maintaining the reaction temperature between about 0° and about 140° C.,
   c) allowing the batch to stand for about 0 to about 3 hours subsequent to separation thereof,
   d) separating the organic from the aqueous phase, and
   e) obtaining the product by distilling the solvent off.

2. The method of claim 1, wherein the temperature is maintained at a temperature between about 20° to about 60° C.

3. The method of claim 1, wherein the inert solvent is a solvent that does not react with either organo-tin hydrides or sodium borohydride.

4. The method of claim 1, wherein the bis-trialkyl-tin]oxide and the sodium borohydride are present in a molar ratio of about 1:1.

5. The method of claim 4, wherein the aqueous solution of sodium borohydride is stabilized with a base.

6. The method of claim 5, wherein the base is sodium hydroxide.

7. The method of claim 1, wherein the reduction of the bis-[trialkyl-tin]oxide is accelerated by adding about 0.1 to about 10% by weight of hydrogen-acid compounds.

8. The method of claim 7, wherein the hydrogen-acid compound is thiosalicylic acid, lactic acid, dodecanethiol or thioglycolic acid.

9. The method of claim 8, wherein the hydrogen-acid compound is thioglycolic acid.

10. The method of claim 1 wherein the reduction of the bis-[trialkyl-tin]oxide is carried out in the presence of about 0.01 to about 10% by weight of antioxidants.

11. The method of claim 10, wherein the antioxidant is butylated hydroxytoluene, 3-tert-butyl-4-hydroxyanisole, pyrogallol, triphenylphosphine, 4,4-thio-bis-(2-tort-butyl-5-methylphenyl), ethylenediamine N,N,N',N'-tetra-2-propyl alcohol, or N',N'-diphenyl-1,4-phenylenediamine.

12. The method of claim 1, wherein the inert solvent is diethylether, dioxane, acetonitrile, or hydrocarbons.

13. The method of claim 12, wherein the solvent is tetrahydrofuran.

* * * * *

UNITED STATES PATENT AND TRADEMARK OFFICE
CERTIFICATE OF CORRECTION

PATENT NO. : 5,288,886
DATED : February 22, 1994
INVENTOR(S) : Ralf-Jurgen Becker, et al.

It is certified that error appears in the above-indentified patent and that said Letters Patent is hereby corrected as shown below:

Column 1, line 52: "German, Patent" should read --German Patent--

Column 6, line 9: delete "0"

Column 6, line 39, Claim 4: "bis-trialkyl-tin]oxide" should read --bis[trialkyl-tin] oxide--

Signed and Sealed this

Twenty-third Day of August, 1994

Attest:

BRUCE LEHMAN

Attesting Officer  Commissioner of Patents and Trademarks